(12) United States Patent
Ambrose et al.

(10) Patent No.: US 6,309,886 B1
(45) Date of Patent: Oct. 30, 2001

(54) HIGH THROUGHPUT ANALYSIS OF SAMPLES IN FLOWING LIQUID

(75) Inventors: W. Patrick Ambrose; W. Kevin Grace; Peter M. Goodwin; James H. Jett, all of Los Alamos, NM (US); Alan Van Orden, Fort Collins, CO (US); Richard A. Keller, White Rock, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/449,280

(22) Filed: Nov. 24, 1999

Related U.S. Application Data
(60) Provisional application No. 60/137,656, filed on Jun. 4, 1999.

(51) Int. Cl.$^7$ .................................................. G01N 21/64
(52) U.S. Cl. .......................... 436/63; 436/172; 422/82.08; 356/72; 356/73
(58) Field of Search ................... 436/63, 172; 422/82.08; 356/72, 73; 250/458.1, 459.1, 461.2

(56) References Cited

U.S. PATENT DOCUMENTS

| | | | | |
|---|---|---|---|---|
| Re. 35,868 | * | 8/1998 | Kosaka ................................. | 250/574 |
| 4,786,165 | * | 11/1988 | Yamamoto et al. ................... | 356/23 |
| 5,247,339 | * | 9/1993 | Ogino .................................... | 356/73 |
| 5,436,717 | * | 7/1995 | Ogino .................................... | 356/72 |
| 5,521,699 | * | 5/1996 | Kosaka et al. ........................ | 356/73 |
| 5,558,998 | | 9/1996 | Hammond . | |
| 5,909,278 | * | 6/1999 | Deka et al. ........................... | 356/318 |
| 6,139,800 | * | 10/2000 | Chandler ............................... | 422/82.08 |

OTHER PUBLICATIONS

Peter M. Goodwin et al., "Rapid Sizing of Individual Fluorescently Stained DNA Fragments by Flow Cytometry," Nucleic Acids Research 21, No. 4, 803 (1993).

Mitchell E. Johnson et al., "Sizing of DNA Fragments by Flow Cytometry," SPIE 1895, 69 (1993).

Zhengping Huang et al., "Large DNA Fragment Sizing by Flow Cytometry: Application to the Characterization of P1 Artificial Chromosome (PAC) Clones," Nucleic Acids Research 24, No. 21, 4202 (1996).

Jeffrey T. Petty et al., "Characterization of DNA Size Determination of Small Fragments by Flow Cytometry," Analytical Chemistry 67, No. 10, 1755 (1995).

Raymond Mariella, Jr., et al., "Flow–Stream Waveguide for Collection of Perpendicular Light Scatter in Flow Cytometry," Cytometry 24, 27 (1996).

* cited by examiner

Primary Examiner—Jeffrey Snay
(74) Attorney, Agent, or Firm—Ray G. Wilson

(57) ABSTRACT

Apparatus and method enable imaging multiple fluorescent sample particles in a single flow channel. A flow channel defines a flow direction for samples in a flow stream and has a viewing plane perpendicular to the flow direction. A laser beam is formed as a ribbon having a width effective to cover the viewing plane. Imaging optics are arranged to view the viewing plane to form an image of the fluorescent sample particles in the flow stream, and a camera records the image formed by the imaging optics.

13 Claims, 4 Drawing Sheets

HIGH THROUGHPUT ANALYSIS OF SAMPLES IN FLOWING LIQUID

RELATED APPLICATIONS

This application claims the benefit of U.S. Provisional Application No. 60/137,656, filed Jun. 4, 1999.

STATEMENT REGARDING FEDERAL RIGHTS

This invention was made with government support under Contract No. W7405-ENG-36 awarded by the U.S. Department of Energy. The government has certain rights in the invention.

FIELD OF THE INVENTION

The present invention relates generally to the problem of increasing sample throughput and analysis for fluorescence based flow cytometry, and, more particularly, to DNA fragment sizing using flow cytometry as the flow-based luminescence system.

BACKGROUND OF THE INVENTION

DNA fragment sizing is one of the most widely used analytical techniques in the biological, biomedical, and forensic sciences, and is becoming increasingly important in the environmental sciences, as well. Techniques for DNA sequencing, DNA fingerprinting, restriction mapping, and genotyping all rely on the ability to accurately determine the size distribution of DNA fragments in a multicomponent solution. Gel electrophoresis is currently the standard analytical tool for sizing DNA. Conventional gel electrophoresis possesses single base pair (bp) sizing resolution for 10 to ~700 bp DNA and can measure fragments as large as a few tens of kilobase pairs (kbp) with a sizing resolution of ~10%. Fragments ranging from tens to hundreds of kbp can be sized using pulsed field gel electrophoresis (PFGE) with ~10% sizing resolution. These techniques provide accurate information that is widely accepted. However, there are increasing demands for DNA sizing methods with higher speed and better sensitivity than gel electrophoresis can provide. To meet these demands, a number of groups are developing novel approaches to DNA sizing, based on such techniques as single molecule fluorescence burst detection, capillary electrophoresis, optical mapping, mass spectrometry, and atomic force microscopy.

Fluorescence burst detection of single DNA molecules labeled with fluorescent intercalating dyes has shown significant improvements in the speed and sensitivity of DNA fragment sizing compared to gel electrophoresis, particularly for the sizing of DNA fragments in the size range of hundreds of bp to hundreds of kbp. The quantity of fluorescent dye intercalated into a DNA fragment is directly proportional to its length. Thus, assuming that each fragment experiences the same excitation intensity, the number of fluorescence photons detected per fragment (burst size) is a direct measure of the DNA fragment size. The DNA fragment sizing technique that has been developed at Los Alamos National Laboratory, referred to as single molecule flow cytometry (SMFC), has been demonstrated to size femtogram (fg) quantities of >300 bp to 425 kbp DNA in a complex mixture of DNA fragment sizes after several minutes of data acquisition and analysis. This is compared to the nanogram (ng) quantities of DNA and the analysis tirhes of several hours required for DNA fragment sizing by gel electrophoresis. For fragments >20 kbp, the sizing resolution obtained by SMFC is similar to PFGE, and the accuracy is better (2% versus 10% uncertainty). In addition, the burst sizes are linear with fragment size. DNA fragment sizing by SMFC has recently been applied to the characterization of P1 artificial chromosome (PAC) clones, the analysis of PCR fragments, and bacteria fingerprinting.

In spite of the substantial improvements in the speed and sensitivity of DNA fragment sizing by SMFC, there are numerous applications in the biomedical and environmental sciences that would benefit greatly from even higher sample throughput for sizing trace quantities of DNA present in large sample volumes or for rapidly characterizing large numbers of samples. The sample throughput provided by conventional SMFC is limited to a maximum burst detection rate of ~100 fragments per second by the finite transit time (~2 ms) of the DNA fragments through the detection region needed to acquire a sufficient number of photoelectrons per fragment for adequate counting statistics. Increasing the sample delivery rate beyond ~100 fragments per second results in a high incidence of events corresponding to double occupancy of the detection region, while decreasing the transit time reduces the burst sizes and thus degrades the resolution. The laser irradiance cannot be increased to compensate for a shorter transit time because the fluorescence becomes optically saturated. Optical saturation is the limited fluorescence rate due to ground state depletion caused by finite excited state lifetimes.

The present invention is directed to a new approach to detecting particles in biochemistry that, in its present configuration, has demonstrated the measurement of thousands of DNA fragments per second, resulting in more than an order of magnitude increase in the sample throughput compared to conventional SMFC. The volumetric flow rate of the analyte solution was increased to 2.5 $\mu$l/min, compared to a typical value of ~0.2 $\mu$l/min for the conventional approach. This increase in sample throughput was accomplished by combining SMFC with parallel fluorescence imaging detection using a charge coupled device (CCD) camera. Whereas conventional SMFC monitors the fluorescence from a single detection volume, defined by the interaction of a tightly focused laser beam and the image of an aperture at the laser focus, this new approach simultaneously monitors thousands of detection volumes, defined by the number of pixels in the CCD array.

This technique has been applied to the detection and sizing of individual DNA-dye complexes in the 7 to 154 kbp size range, although much larger or smaller fragments can be analyzed in this way. As with fragment sizing by conventional SMFC, the burst sizes were linear with DNA fragment size. Unlike conventional SMFC, data sufficient to determine the DNA fragment size distribution were acquired in less than 10 seconds. At present, the smallest DNA-dye complex that can be detected with a signal-to-noise ratio of ~2 is 1.86 kbp. A measurement rate as high as $10^5$ DNA fragments per second can be achieved by using a faster detector than the one used in the initial experiments, while still maintaining this same level of sensitivity.

Various objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

As embodied and broadly described herein, the present invention includes apparatus and method for imaging multiple fluorescent sample particles in a flow channel. A flow channel defines a flow direction for samples in a flow stream and has a viewing plane perpendicular to the flow direction. A laser beam is formed as a ribbon having a width effective to cover the viewing plane. Imaging optics are arranged to view the viewing plane to form an image of the multiple fluorescent sample particles in the flow stream and a camera records the image formed by the imaging optics.

BRIEF DESCRIPTION OF THE DRAWINGS

The accompanying drawings, which are incorporated in and form a part of the specification, illustrate the embodiment(s) of the present invention and, together with the description, serve to explain the principles of the invention. In the drawings.

DETAILED DESCRIPTION

In accordance with the present invention, parallel detection is accomplished with a charge coupled device (CCD) camera (a CCD camera is a light detector consisting of an array of many detectors). Briefly, the invention involves 1) a liquid sample flowing in a channel, 2) illuminating the channel cross section with a thin, wide ribbon of laser light, 3) using imaging optics that are in line with and view into the end of the flow channel to collect fluorescence from objects crossing the ribbon of laser light (end-on imaging), and 4) parallel image detection of fluorescence from samples that flow towards the detector and across the laser beam. This technique is particularly valuable for single particle (e.g., cells, chromosomes, single molecules, and the like) detection and counting applications in which high speed throughput and low cost, compact instrumentation are of importance.

Figure 1:
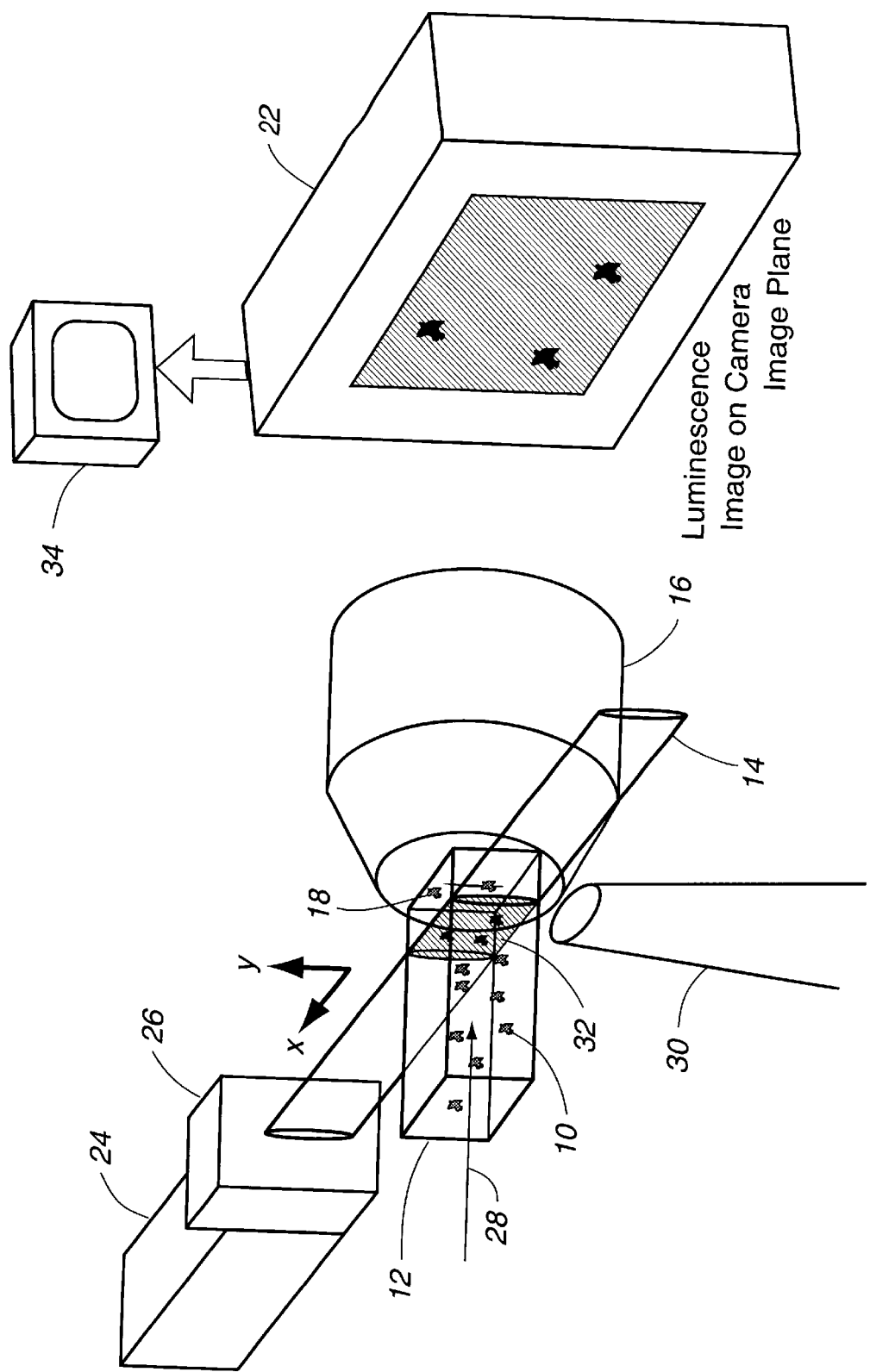
FIG. 1 is a schematic of one embodiment of apparatus used for parallel fluorescence imaging in single molecule flow cytometry (SMFC).

To overcome the problem of fundamentally photon-emission-rate limited sample detection from one sample at a time, the present invention provides a method to observe many individual optical signals concurrently. FIG. 1 shows the basic scheme for parallel detection of fluorescence in flow. This basic scheme involves 1) flowing a dilute sample 10 throughout the entire cross section of a flow channel 12, 2) passing sample 10 through a thin, wide ribbon or sheet of laser light 14, 3) using imaging optics 16 to collect and image fluorescence light emitted from each object 18 in the flow direction (fluorescent objects 18 flow towards the detectors 22), i.e., imaging the flow cell 12 "end on", and 4) using a parallel array of detectors 22 to observe the fluorescence from many objects 18 separately and concurrently. After passing through viewing plane 32, the sample stream is removed through sample drain 30.

In a particular embodiment of the apparatus, the parallel array of detectors 22 was a slow-scan, cooled CCD camera with low dark charging rate and low readout noise. The camera consisted of an array of 1242×1152 CCD pixel elements. The ribbon of laser light 14 in the middle of flow cell 12 was generated by focusing a beam from laser 24, e.g., an argon ion laser beam, with two crossed cylindrical lenses 26 with focal lengths of 1 m and 25 mm to $1/e^2$ diameters of approximately 200 and 10 $\mu$m, respectively. The light collection and imaging optics 16 looking into the end of flow cell 12 was an infinity corrected, 1.0 Numerical Aperture 100×water-immersion objective. A 50-mm camera lens (not shown) was used to reform and image on CCD camera 22.

In a particular embodiment of the SMFC instrument generally described above, a 20 mW, 514 nm continuous wave laser beam from an air-cooled $Ar^+$laser 24 (American Lasers, Salt Lake City, Utah) was shaped into a planar sheet and focused into a 250×250 $\mu m^2$ flow channel, ~1 mm from the outlet, using 1000 and 25 mm focal length cylindrical lenses 26 oriented parallel and perpendicular to the flow axis 28 of sample stream 10, respectively, to form a ~10 $\mu$m×~200 $\mu$m×250 $\mu$m excitation region for viewing plane 32. Femtomolar (fM) solutions of fluorescently labeled DNA were delivered into flow cell 12 by a syringe pump (not shown) at a volumetric flow rate of 2.5 $\mu$l/min, corresponding to a transit time of ~4 ms for single molecules in the center of flow cell 12. Viewing plane 32 was imaged onto a thermoelectrically cooled slow-scan CCD camera 22 (EEV 1152×1242, 1 MHz readout, 12 bit digitization, Princeton Instruments, Princeton, N.J.) using a 100×, 1.0 NA water immersion objective 16 (Zeiss, Germany) and 50-mm camera lens (Nikon, Japan). Fluorescence was collected through a 550±15 nm optical bandpass filter (not shown) (Omega Optical, Brattleboro, Vt.). Data from the CCD camera were acquired using a PC computer 34 interface and data acquisition software from Princeton Instruments and analyzed off line using IDL software (Research Systems, Boulder, Colo.) running on a Sun workstation. The x and y axes refer to the axial and radial dimensions of the laser beam, respectively.

Figure 2A:
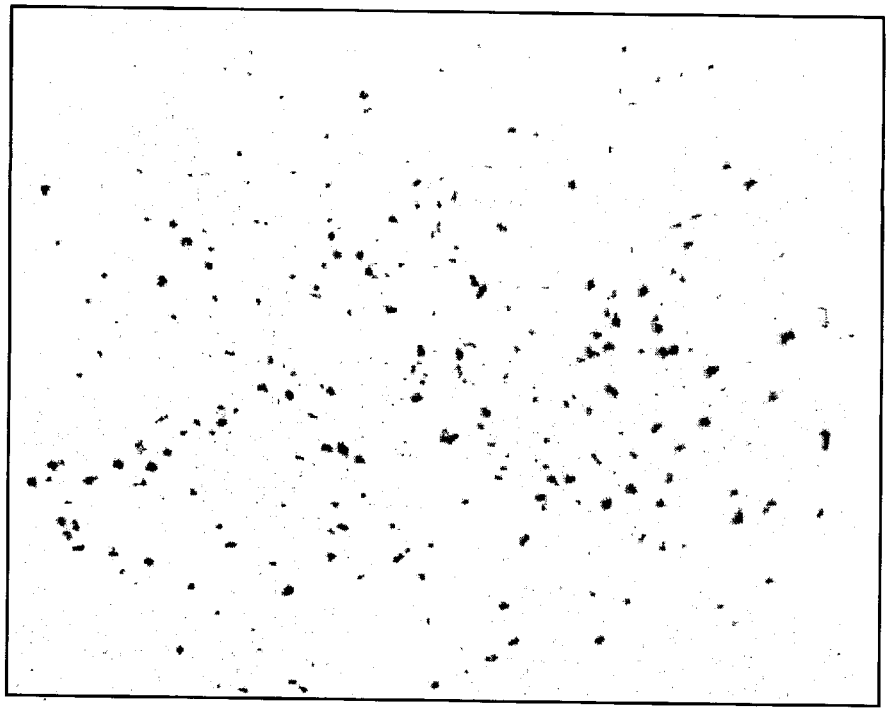
FIGS. 2A and 2B are pictorial displays of two consecutive CCD camera images obtained from a continuously flowing solution containing a mixture of DNA fragments.
Figure 2B:
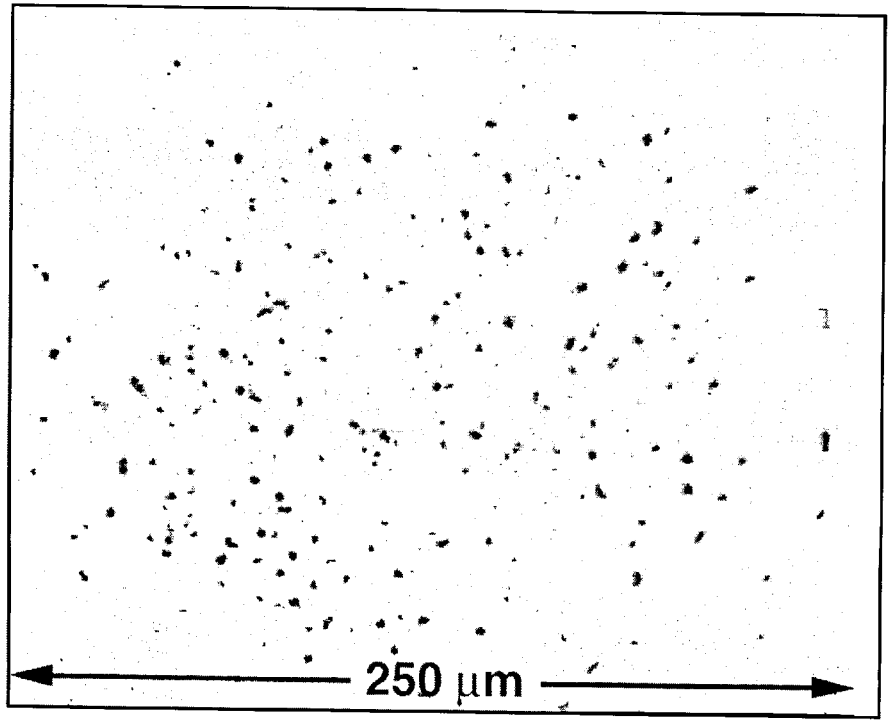

FIGS. 2A and 2B display two consecutive CCD camera 22 (FIG. 1) images obtained from a continuously flowing solution containing a mixture of 7.2, 48.5, and 154 kbp DNA, labeled with the bisintercalating dye TOTO-1, at a DNA concentration of ~$10^{-15}$ M. The DNA sample consisted of M13RF DNA (7249 bp) and bacteriophage $\lambda$DNA (48502 bp) purchased from Life Technologies (Gaithersburg, Md.) and a bacterial artificial chromosome (BAC) clone obtained from the Life Sciences Division, Los Alamos National Laboratory. The size of the BAC clone was determined independently to be 154.2±5 kbp by conventional SMFC and confirmed using restriction digestion and gel electrophoresis. Solutions of ~$10^{-12}$ M DNA in TE buffer (10 mM Tris-HCl, 0.5 mM EDTA, pH 8) were stained with the dimeric fluorescent intercalating dye TOTO-1 (Molecular Probes, Eugene, Oreg.) at a dye/bp ratio of 1:5. After 1 hr, the stained solutions were diluted to ~$10^{-15}$ M in TE buffer.

The dark spots shown in FIGS. 2A and 2B are due to bursts of photons emitted by individual DNA-dye complexes as they flow through the excitation region and viewing plane out of the plane of the page. Each image was obtained with an exposure time of 150 ms and a camera readout time of 280 ms. To limit the fraction of bursts truncated at the end of the exposure, the flow rate of the analyte solution was adjusted so that the average transit time for fragments in the center of the flow cell was ~4 ms. Thus, each exposure integrates over many single fragment transits both spatially and temporally. An average of ~1000 DNA fragment bursts were detected per image, which corresponds to a detection rate of ~2000 fragments per second, currently limited by the long readout time of the experimental CCD camera.

The burst sizes for a given DNA fragment size vary across the excitation region because of spatial variations in the laser intensity, the optical collection efficiency, and the flow velocity profile. For example, because of the parabolic flow profile that is characteristic of pressure driven systems, DNA fragments flowing near the walls of the flow channel have longer transit times through the laser beam than fragments flowing through the center, giving rise to a disproportionately large number of photoelectrons for the same sized fragment. To correct for these effects, the average burst size of the 154 kbp fragment was determined at each pixel for a data set.

Figure 3:
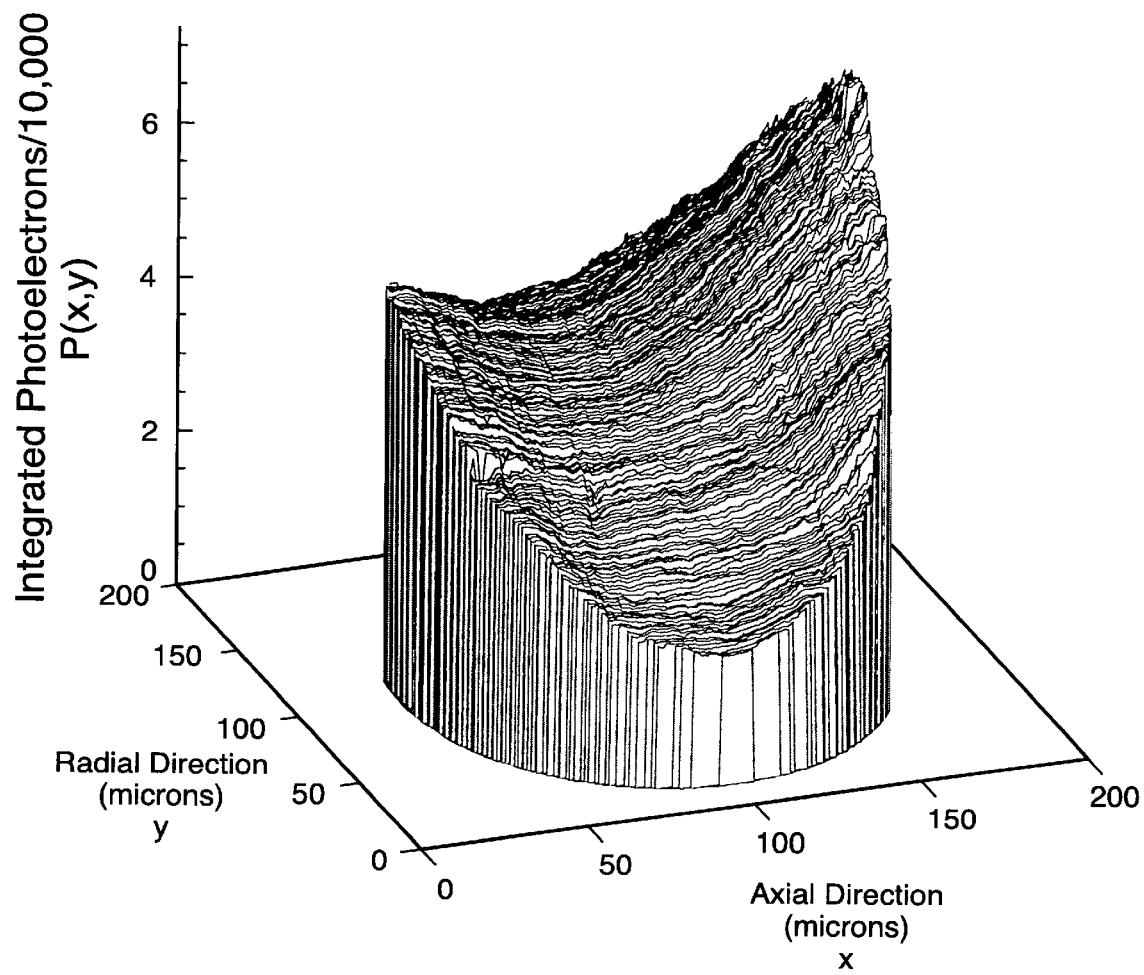
FIG. 3 graphically depicts a calibration surface for correcting spatial variations in the flow rate and the excitation and optical collection efficiencies across the excitation region, where x and y are axial and radial displacements along the laser beam, respectively.

A calibration surface, P(x,y), shown in FIG. 3, was used to correct for the spatial variations in the flow rate and the excitation and optical collection efficiencies across the excitation region, where x and y are axial and radial displacements along the laser beam, respectively. One hundred consecutive images were acquired under identical conditions to those described for FIG. 2. The burst sizes, S(x,y), were obtained by subtracting the background from each image, identifying the locations of peaks above a threshold value (~70 photoelectrons in one pixel), and integrating the number of photoelectrons in each peak. Histograms of burst sizes, H(x,y), were constructed within 37×37 pixel boxes about each (x,y). The mean burst size, P(x,y), for the largest fragment was determined in each H(x,y) using a fit to a Gaussian peak plus linear background.

The calibration surface has a saddle point at the intersection of the maximum laser intensity and flow profiles. In the axial dimension of the laser beam, the calibration surface rises from the saddle point because the transit times for molecules in the center of the flow channel are shorter than for those near the walls. The calibration surface falls off from the saddle point in the radial dimension of the laser beam because of the fall off in the laser beam intensity in this dimension. The asymmetric shape of P(x,y) is due to the imperfect alignment of the laser beam with respect to the flow cell.

Figure 4A:
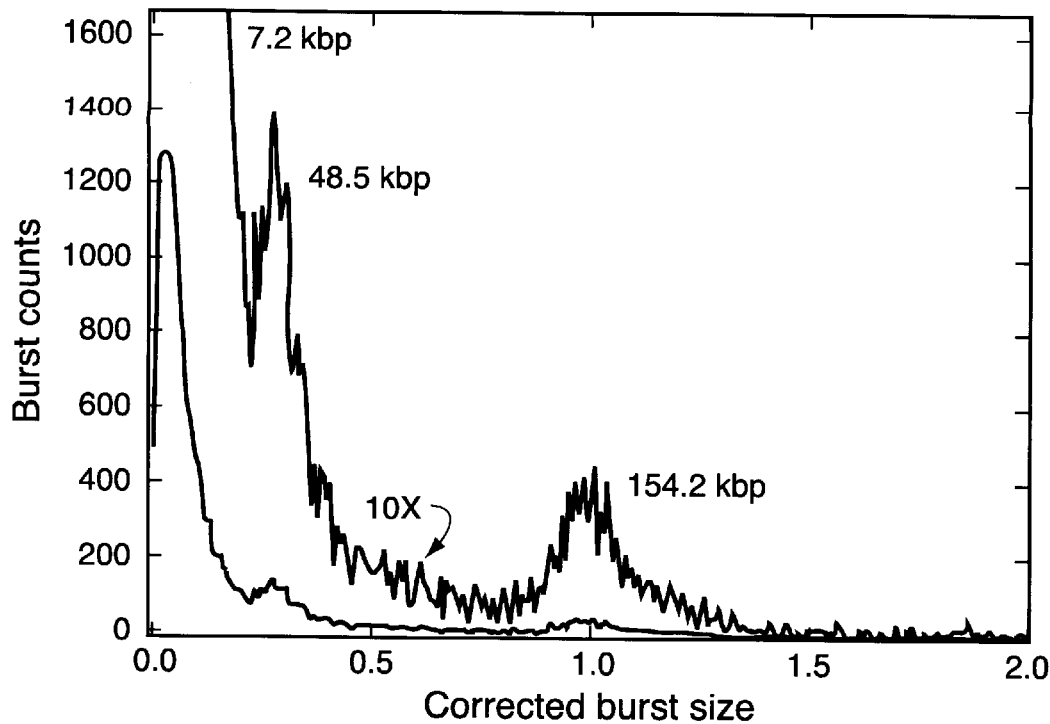
FIG. 4A is a corrected burst size distribution obtained from the apparatus shown in FIG. 1.

The corrected burst size distribution (BSD) in FIG. 4A was obtained from 20 consecutive images using the conditions described for FIG. 2 with a data acquisition time of 8.6 seconds. The data analysis time was ~1 minute per image. With highly parallel computing, this data time can be further reduced. The burst sizes S(x,y) were determined as described above, rescaled using S(x,y)/P(x,y), and histogrammed to give the corrected BSD shown in FIG. 4A. The burst size distribution is shown also on an expanded vertical scale (110×) for clarity. Three well-resolved peaks are observed in the BSD corresponding to the three different DNA fragment sizes. The peak position for the smallest fragment does not depend lo on the threshold value, which was verified by analyzing the data using different threshold values.

Figure 4B:
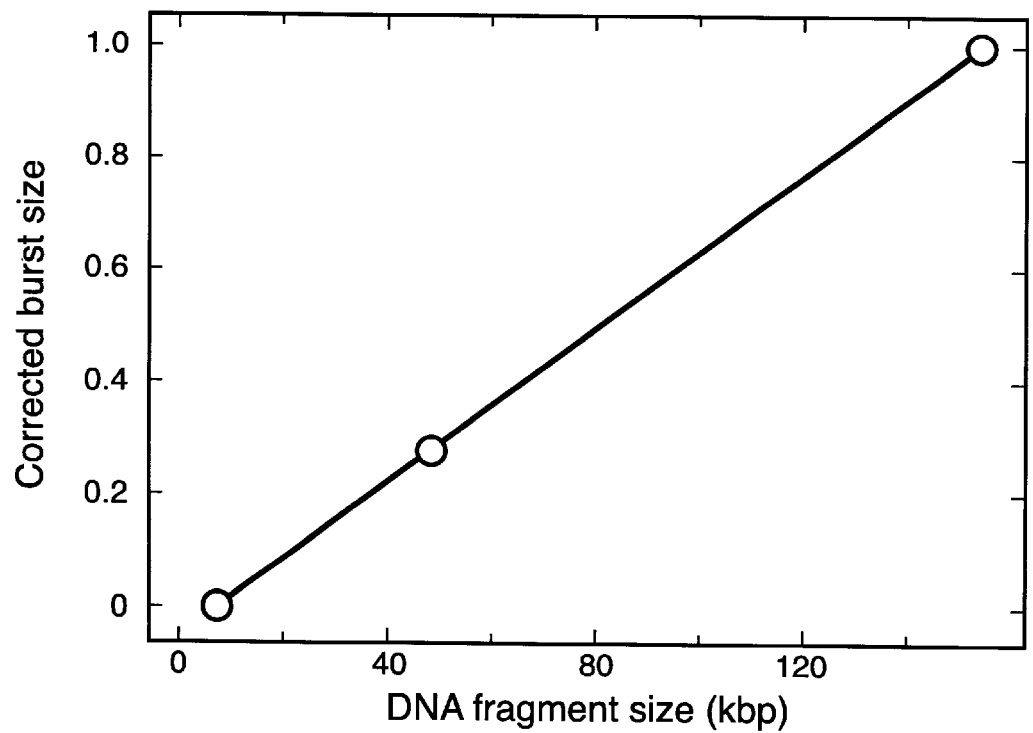
FIG. 4B is a plot of the centroids of the peaks shown in FIG. 4A vs. DNA fragment size.

FIG. 4B displays the linear relationship between the DNA fragment size and the peak positions in the BSD, having a correlation coefficient $r^2$=0.999985, obtained by fitting each peak with a Gaussian function. The sizing resolution is characterized by the coefficient of variance (CV), given by CV=100×$\sigma/\bar{x}$, where $\sigma$ is the standard deviation and $\bar{x}$ is the centroid of the peak in the BSD. From Gaussian fits to the peaks in FIG. 4A, CVs obtained were ~50%, 11%, and 7% for the 7.2, 48.5, and 154 kbp DNA fragments, respectively. As with the conventional SMFC approach to DNA fragment sizing, the CV decreases with increasing fragment size because of the increasing number of detected photons, $\bar{x}$. The CVs reported here for the larger fragments are comparable to those observed using PFGE but are a factor of ~3 larger than those obtained by conventional SMFC.

By examining FIG. 3, it is seen that the number of photoelectrons measured for one 154.2 kbp fragment is in the range of $2\times10^4$ to $6\times10^4$. In the absence of excessive background noise and other technical noise sources, the signal-photon, shot-noise limited width should be similar to $100\sqrt{2\times10^4}/2\times10^4$=0.7 percent. The larger widths in the exemplary demonstration are due in part to the presence of excess noise sources compared with the more conventional approach. One source of excess noise arose from the need to reduce the fraction of bursts that were truncated at the edges of an image integration period. An integration time 38 times longer than the minimum transit time was used. Hence, background interference from scattered laser light and fluorescent impurities was integrated up to 38 times longer than the transit time of a single fragment and resulted in larger widths.

The principle demonstrated with the present experimental setup is that parallel detection of many fluorescently labeled DNA fragments increases the sample throughput by more than an order of magnitude compared to conventional SMFC. The long readout time of the CCD camera used for these experiments prevented further increase in the sample throughput. Using a commercially available frame transfer CCD camera for detection will essentially eliminate the readout time and enable continuous monitoring of the detection region. The entire area of such a camera can be utilized, making it possible to enlarge the detection region and increase the volumetric flow rate of the sample. Finally, the integration time can be matched with the transit time, resulting in improved detection sensitivity and sizing resolution. Given these considerations, the detection rate can be increased to as high as $10^5$ fragments per second, using improvements discussed below, with a sensitivity of a few kbp. This will result in a detection rate that is comparable to that of commercially available flow cytometers used for single cell analysis, but with significantly higher sensitivity.

The above laboratory results demonstrate the application of parallel fluorescence imaging to high throughput DNA fragment sizing by SMFC. For example, there is a current need for field portable techniques that can be used to rapidly identify DNA from bacteria and other organisms in environmental samples. The DNA fragment sizing technique described here is ideally suited to this application because of its ability to rapidly detect and size trace quantities of DNA in large sample volumes.

Another application for this technique is to characterize artificial chromosome clone libraries. Such libraries are widely used in gene mapping, DNA sequencing, and other types of genome analysis and can consist of as many as hundreds of thousands of DNA clones in microtiter wells, ranging in size from tens to hundreds of kbp. The technique of the present invention provides the ability to analyze each library component in only a few seconds and will thus permit the entire library to be characterized much more rapidly than can be accomplished with PFGE.

A main advantage of the present invention is that parallel detection increases sample throughput. The preliminary laboratory results described above demonstrate a factor of 20 higher sample analysis rate for DNA fragments compared with detection of one-fragment-at-a-time (about 2000 fragments per second compared with 100 fragments per second).

An advantage of this method of flow analysis is that the sample moves in a flow channel without the need for injection capillaries and hydrodynamic sample focusing within a sheath flow. Many types of flow cytometry use a narrow sample injection capillary to produce a thin sample stream within a larger sheath flow channel. Use of a large diameter flow channel with a larger volume to surface ratio will reduce problems associated with sample adhesion to the walls, reduce sample degradation by interaction with the walls, reduce capillary clogging events, and reduce shearing of DNA fragments.

An advantage of the present system is the use of high numerical-aperture imaging optics, which, when combined with a CCD, provide a smaller probe volume. The optical background is proportional to the probe volume. In a one-at-a-time system, the probe volume must be larger than a fluorescent object in the sample.

For end-on imaging with a camera, the effective sample probe volume is reduced to the demagnetized image size of a piece of DNA (or other fluorescent object). It is estimated that the probe volume is reduced from 10×10×10 to 1×1×10 $\mu m^3$. Hence, the optical background rate is expected to be reduced by a factor of 100 compared to DNA fragment sizing using a single detector and single probe volume. In the examples above, the integration time was much longer than the transit time. This was done to reduce the fraction of bursts that are truncated at the ends of the integration time (e.g., in the middle of the flow channel, the fraction of truncated bursts is expected to be (4.5 ms)/(150 ms)=3%). Under these conditions the optical background is larger than if the integration time was comparable to or less than the transit time. A variation on the implementation of parallel detection using a different camera removes this disadvantage.

A high sensitivity frame-transfer camera and high speed image acquisition and processing system can be used to enhance the sample throughput over the preliminary demonstration. Examples of such hardware are:

1M15 Camera from Silicon Mountain Design, Colorado Springs, Colo. 80919

Digital Recording System with Real Time Image Processing (Matrox Genesis) from Bosque Computing, Albuquerque, N.Mex. 87198 The 1M15 camera has the following specifications:

1000×1000 pixel frame transfer CCD camera.

Preset image acquisition rates of 15 or 7.5 frames per second or an adjustable frame rate slower than 7.5/sec with external triggering (shortest integration time 67 ms)

250 nanosecond transfer of the image charge to a CCD storage area (negligible compared with the image acquisition time)

Readout of the stored image during subsequent integration period (no readout dead time)

55 e- RMS readout noise 12 bit ADC

Gain selectable 1× or 4× (one quarter of the full well digitized).

Full well 300,000 photoelectrons.

The detection rate for DNA fragment sizing by SMFC with parallel imaging is expected to increase to ~$10^5$ fragments per second with a sensitivity of a few kbp by using the above commercially available frame transfer CCD camera instead of the slow-scan camera used to obtain the exemplary results. The frame transfer camera would essentially eliminate the readout time and enable continuous monitoring of the detection region. Continuous imaging avoids the problem of truncated bursts, and the image integration time and shortest transit times can be matched, resulting in improved signal-to-background ratio, detection sensitivity, and resolution. Eliminating the readout dead time increases the number of images per second by more than a factor of three. The entire area of a camera with approximately 1000×1000 pixels can be utilized, making it possible to enlarge the detection region and increase the volumetric flow rate of the sample by a factor of 10 (1000×1000 pixels/335×289 pixels). Hence, with a change of apparatus the measurement rate can be increased by the product of enhancements ((2000 fragments per image)×(10 times larger flow channel area and image area)×(at least 3 times more images per second)) to ~$10^5$ fragments per second. In order for the numerical analysis rate to keep up with data rate, a dedicated system of parallel image processors will need to be developed. The detection rate that is projected is comparable to that of commercially available flow cytometers used for the analysis of single cells, and the like, but the sensitivity will be much higher.

Other methods of calibration are possible. In the present demonstration, a calibration standard was used to obtain information about the brightness per transit at different positions in an image. To reduce the errors associated with this calibration method, a much larger sampling of the calibration sample is desired (perhaps 100 times as much calibration data or more). Obtaining much more calibration data could become impractical for some applications, especially when calibration is needed frequently. The calibration needs to account for 1) information on the optical parameters of the combined apparatus at each position, and 2) information on the transit time at each position. In the first calibration method described above, the photon bursts measured for individual calibration sample objects (e.g., individual DNA fragments) contain both the optical and transit time information. The optical information alone could be obtained separately by imaging the luminescence from a highly concentrated sample, such as a dye solution or the background from unbound dye in the sample images. Such an image does not contain transit time information.

The transit time field in a flow channel is inversely proportional to the flow velocity field. The velocity field can be calculated. Hence, a second calibration method is to obtain a dye image and multiply this by the calculated transit time field.

A third calibration method to flatten spatial variations is a mixture of the first and second methods. Instead of using a calculation for the flow velocity and transit time, a surface fitting method can be used to obtain an estimate for the transit time. The transit time can be estimated by a polynomial surface function (e.g., T(x,y)=sum of terms such as $A_{mn}x^m y^n$ with m,n=0,1,2,3 . . . ). T(x,y) is multiplied by the optical dye image, and this can be fitted by a suitable minimization algorithm (least squares minimization or maximum likelihood methods) to a representative sampling of calibration-sample burst images. The resulting product surface is the calibration surface.

Another enhancement of the present invention will be to detect more than one color at once. Tags or dye molecules of different colors attached to the same sample object can be used to obtain coincidence detection of different parameters in the sample. For example, the size of a DNA fragment can be determined by the brightness of an intercalating dye, and specific fragments can be identified simultaneously by additional hybridization probes of a different color. As another example, an internal standard could be run simultaneously with the sample.

Several methods for multicolor detection are possible. One or several laser excitation wavelengths can be used. In one method, dichroic beam splitters could be used to split portions of an image at different emission wavelengths into different optical paths, and to image these different images onto different parts of the same camera, or onto different cameras. In another method for multicolor detection, several laser excitation wavelengths will be used, the laser colors will be chopped alternately in time, and synchronous detection will be performed in one camera. The timing of the emission to the laser "on" periods will then be used to determine the colors.

Other modifications that will enhance the analysis involve reducing the variation of flow velocities across the measurement region. The calibration methods described above can be a large source of error since the calibration image can have largely different values across an image. One way to reduce the possible sources of error is to reduce the range of calibration values needed. A larger flow channel (e.g., 2 mm ×2 mm), a wider laser beam (e.g., 10 $\mu$m×2 mm at the focus), and imaging a smaller fraction of the flow field in the middle of the channel (e.g. 500×500 $\mu$m$^2$) will reduce the variations of the transit times across the image. Without a sample introduction capillary, not all of the sample will be measured. In cases where all of the sample must be measured, a large diameter sample introduction capillary may be used to provide a source of weak hydrodynamically focused flow in the middle of a large channel (e.g. comparable to 500×500 $\mu$m$^2$ cross section).

Another method for accomplishing a reduction of variation in velocities across the flow channel is to replace pressure flow with electrokinetic flow.

Electrokinetic flow is characterized by an approximately flat flow profile across a flow channel compared with an approximately quadratic dependence on position for pressure flow.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for imaging multiple fluorescent sample particles in a flow channel comprising:

a flow channel defining a flow direction for samples in a flow stream and having a viewing plane perpendicular to the flow direction;

a laser beam formed as a ribbon having a width effective to cover the viewing plane; and imaging optics arranged to view the viewing plane to form an image of the multiple fluorescent sample particles in the flow stream; and a camera to record the image formed by the microscope objective.

2. Apparatus according to claim 1, wherein the camera is a CCD camera.

3. Apparatus according to claim 2, wherein the CCD camera is a frame transfer CCD camera.

4. Apparatus according to claim 1, further, including beam shaping optics for forming the ribbon laser beam.

5. Apparatus according to claim 1, wherein the imagining optics comprises a microscope objective.

6. Apparatus according to claim 4, where the beam shaping optics comprise crossed cylindrical lenses.

7. A method for imaging multiple fluorescent sample particles in a flow stream, comprising the steps of:

flowing the flow stream throughout a flow area of a flow channel;

forming a ribbon laser beam that is perpendicular to and illuminates the flow area along an image plane;

passing the sample particles through the ribbon laser beam to excite the sample particles; and collecting the florescence light emitted from each sample particle within the image plane to form an image of the multiple fluorescent sample particles in the flow area.

8. A method according to claim 7, further including the step of recording the image on a CCD camera.

9. A method according to claim 8, further including the steps of:

integrating the image on pixels of the CCD camera for a first image period; and reading out charge collected on the pixels to complete a first data acquisition cycle.

10. A method according to claim 7, further including the step of calibrating the image for particle velocity variations across the flow area.

11. A method according to claim 7, further including the step of calibrating the image to account for optical variations over positions in image field and particle transit times over the positions in image field.

12. A method according to claim 7, further including the step of labeling different particles with different fluorophores that fluoresce at different characteristic wavelengths.

13. A method according to claim 12, further including the step of forming the ribbon laser beam with a plurality of laser excitation wavelengths.

* * * * *